United States Patent
Keller

(10) Patent No.: US 6,416,551 B1
(45) Date of Patent: Jul. 9, 2002

(54) INTERVERTEBRAL ENDOPROSTHESIS WITH A TOOTHED CONNECTION PLATE

(75) Inventor: Arnold Keller, Kayhude (DE)

(73) Assignee: Waldemar Link (GmbH & Co.), Hamburg (DE)

( * ) Notice: Subject to any disclaimer, the term of this patent is extended or adjusted under 35 U.S.C. 154(b) by 0 days.

(21) Appl. No.: 09/573,544

(22) Filed: May 19, 2000

(30) Foreign Application Priority Data

May 21, 1999 (EP) ............................................. 99110053

(51) Int. Cl.⁷ .................................................. A61F 2/44
(52) U.S. Cl. .................................... 623/17.11; 623/17.15
(58) Field of Search ............................ 623/17.11–17.16

(56) References Cited

U.S. PATENT DOCUMENTS

| | | | | |
|---|---|---|---|---|
| 3,840,904 A | | 10/1974 | Tronzo ................. 3/1 |
| 5,401,269 A | * | 3/1995 | Buttner-Janz et al. ... 623/17.11 |
| 5,702,450 A | | 12/1997 | Bisserie ................ 623/17 |
| 6,231,609 B1 | * | 5/2001 | Mehdizadeh ............. 623/17.11 |
| 6,251,140 B1 | * | 6/2001 | Marino et al. .......... 623/17.16 |
| 6,258,125 B1 | * | 7/2001 | Paul et al. ............. 623/17.11 |

FOREIGN PATENT DOCUMENTS

| | | |
|---|---|---|
| DE | 3023353 | 4/1981 |
| EP | 0 176 728 | 4/1986 |
| EP | 0 357 547 | 3/1990 |
| EP | 0 522 999 | 1/1993 |
| EP | 0 560 141 | 9/1993 |
| FR | 2 641 461 | 7/1990 |
| FR | 2 659 226 | 9/1991 |

* cited by examiner

Primary Examiner—David H. Willse
Assistant Examiner—Suzette J. Jackson
(74) Attorney, Agent, or Firm—Morrison & Foerster LLP

(57) ABSTRACT

An implant, in particular an intervertebral endoprosthesis, with a connection plate (3) which is to be fixed so as to bear on a bone surface and which is to be applied to the bone surface in a direction of application running transverse to its main extension. For protection against a shearing force running parallel to its main extension, the connection plate (3) has teeth (6) projecting in the direction of application. These teeth (6) are delimited by surfaces (11, 12, 13) which include a main surface (11) arranged in the direction of application and transverse to the direction of shearing. Two teeth or groups of teeth in each case lie opposite one another in the direction of shearing and point in opposite directions.

13 Claims, 2 Drawing Sheets

INTERVERTEBRAL ENDOPROSTHESIS WITH A TOOTHED CONNECTION PLATE

BACKGROUND OF THE INVENTION

An intervertebral endoprosthesis is known (EP-B-176,728) which consists of two connection plates which between them enclose a core. The connection plates are intended to bear on the upper plates of the vertebral bodies on either side. To ensure that the prosthesis does not lose its predetermined position between the vertebral bodies as a result of shearing forces which principally occur in the anteroposterior direction parallel to the main extension of the connection plates, the connection plates must be connected to the vertebral bodies in a suitable manner. For this purpose, the edges of the known prosthesis are provided with teeth which project transversely from each connection plate in order to penetrate into the upper plates of the vertebral bodies under the natural force of pressure acting between said vertebral bodies. In this state, they provide resistance to displacement of the connection plates in relation to the upper plates of the vertebral bodies in any given surface direction of the connection plates and vertebral bodies. To ensure that this resistance is relatively great, the teeth, in the practical design of, said endoprosthesis which has become familiar through use, are arranged transverse to the direction of the surface extension of the connection plates and upper plates. They are in fact delimited by a pair of essentially triangular main surfaces which are attached to the connection plate along their essentially parallel base sides and whose free tip lying opposite the base side points away from the connection plate. For the teeth to have sufficient stability, they are designed with a certain thickness which corresponds to the distance between the triangular surfaces lying parallel to one another. The edges of the triangular surfaces, which extend between the base side and the tip, are connected to each other by rectangular, plane surfaces which converge toward the tooth tip and there form a ridge.

When using the prosthesis, it has been found that the teeth in many cases do not penetrate sufficiently deeply into the upper plates of the vertebral bodies. There is then a risk that they will not be able to correctly perform their function, namely that of holding the prosthesis in the intended position. Experience has shown that in such cases recourse must be made to the use of prosthesis pegs which are inserted into holes which have been drilled beforehand in the vertebral bodies (DE-C-3,023,353, FR-A-2,659,226). However, such working of the vertebral bodies is difficult. It prolongs the operation and weakens the vertebral bodies. The use of pointed, pyramid-shaped teeth is ruled out because the teeth become thicker towards the base, for the purpose of tooth stability, and are accordingly delimited by oblique surfaces, which, in the event of shearing forces, leads to the teeth lifting from the bone.

The object of the invention is to develop the intervertebral endoprosthesis mentioned in the introduction in such a way that the teeth penetrate sufficiently securely into the upper plate of the respective vertebral body and are also securely anchored therein against the effect of shearing forces.

SUMMARY OF THE INVENTION

Accordingly, an intervertebral endoprosthesis is proposed which has a connection plate which is to be fixed so as to bear on a vertebral surface. This connection plate is to be applied to the vertebral surface in a direction of application transverse to its main extension. In order to protect against a shearing force running parallel to its main extension, the connection plate has teeth projecting approximately in the direction of application. These teeth are delimited inter alia by a main surface arranged in the direction of application and transverse to the direction of shearing. In contrast to the conventional, pyramid-shaped tooth configuration, in which the surfaces delimiting the tooth are inclined at the same angle to the direction of application, the teeth according to the invention are designed skew in relation to the direction of application, by means of the fact that the main surface runs parallel to the direction of application and the widening of the tooth from the tip toward its base, as is necessary for its stability, is obtained solely by skewing of the other surfaces.

A non-generic hip-joint endoprosthesis is admittedly known (FR 2,641,461 A1) whose hemispherical part to be anchored in the hip bone provides, on the outer edge, a ring of wedges which converge to a point in the direction of insertion. The outer surfaces of the wedge bodies lie on a cylindrical surface whose cylinder axis runs in the direction of application. However, it remains unclear what technical effect if any is achieved with the cylindrical configuration of the outer wedge surfaces.

The invention is further characterized by the fact that two teeth or groups of teeth in each case lie opposite one another in the direction of shearing and point in opposite directions. This means that the main surfaces of two associated tooth pairs are directed either facing each other or facing away from each other. The reasoning behind this measure lies in the fact that the forces which run transverse to the direction of application, and which are generated when the oblique surfaces penetrate into the vertebra, are oriented in opposite directions and therefore cancel each other out. The teeth can therefore penetrate into the vertebra in the intended direction of application, i.e. in the direction of the main surfaces.

The configuration of the teeth according to the invention has two main advantages. One is that when a shearing force occurs parallel to the main extension of the connection plate, there is always at least one tooth main surface which runs perpendicular to the direction of this shearing force and therefore affords the best conditions for securing the position of the implant against this shearing force. The risk which is present with pyramid-shaped teeth, namely that the implant will be lifted from its bearing position on the vertebra by moving in the shearing direction along an oblique tooth surface, is eliminated.

The second advantage lies in the fact that the vertebral surfaces with which the main surfaces of the teeth cooperate during penetration, and on which they are supported against shearing forces, are spared. Tooth surfaces which run obliquely in relation to the direction of application have the effect that as they penetrate into the vertebral cortex, they cause the latter to gradually break open in order to accommodate the increasing cross section of the penetrating tooth. This breaking impairs the stability of the part of the vertebra concerned. By contrast, at the main surfaces of the tooth which extend in the direction of application, there is no gradual breaking. The parts of the vertebra concerned are therefore spared, remain more stable and better support the tooth. The integrity of the vertebral cortex of the upper plates, and its ability to take up forces, is better preserved in the area of the penetrating teeth, and for this reason it is generally possible to dispense with additional securing means such as screws.

This is especially true if the edges of the main surface are sharp, so that as they penetrate into the bone they cut the latter rather than break it open. If the main surface is plane, the sharpness of the edges of the main surface can be obtained by those surfaces of the tooth which are adjacent to the main surface being arranged at an acute angle (in a cross section parallel to the main extension of the connection plate). The base of the tooth is in this way given, for example, a triangular or trapezoidal configuration. However, it is not absolutely necessary for the main surface to be plane; instead, it can also be made up of two or more plane surfaces adjoining each other at a preferably obtuse angle, or it can be designed with a more or less uniform curvature.

The direction of application is the direction at which one would normally seek to apply the implant to the vertebra. If the connection plate is flat, it is normally perpendicular to the plane of the vertebral plate. If the connection plate is curved, the direction of application is generally by nature perpendicular to the average direction of extension of the connection plate. It can also be seen from the product as the direction at which the main surfaces run parallel to each other.

The shearing forces against which the teeth are intended to hold the intervertebral endoprosthesis on the vertebra generally occur as components of irregularly directed forces, with force components in the anteroposterior direction being particularly high and posing a particular threat to the fixing of the implant on the vertebra. It is therefore particularly important to fix the connection plates in the anteroposterior direction relative to the upper plates of the vertebral bodies. The main surfaces of the teeth provided on the connection plates of the implant are therefore oriented in the A-P direction and in adjoining directions. It is recommended to provide two groups of teeth, of which one group provides support against the anteriorly directed forces and the other group provides support against the posteriorly directed forces. These groups are arranged pointing in opposite directions in such a way that the forces running transverse to the direction of application, and generated by their oblique surfaces as they penetrate into the bone, essentially cancel each other out.

In this connection, a symmetrical arrangement in relation to an axis of symmetry extending transverse to the direction of the shearing force, or in relation to a mirror-symmetrical centre point, may be particularly suitable; however, symmetry is not necessary.

BRIEF DESCRIPTION OF THE DRAWINGS

Further features of the invention will become evident from the following description of an illustrative embodiment which is represented in the drawing, in which.

DETAILED DESCRIPTION OF THE INVENTION

Figure 1:
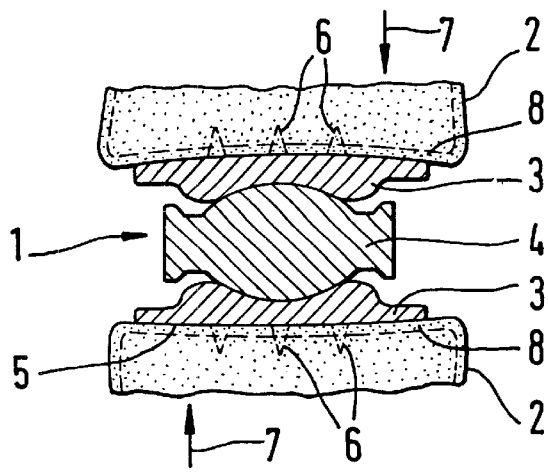
FIG. 1 shows a cross section, viewed from the dorsal or ventral direction, through an intervertebral endoprosthesis arranged between two partially represented vertebral bodies.

The intervertebral endoprosthesis 1 which is to be inserted between two vertebral bodies 2 consists of two connection plates 3 and a core 4. The outer sides 5 of the connection plates 3 have a plurality of pointed teeth 6 which, by means of a force acting in the direction of arrow 7, and possibly also including the natural pressure force acting between the vertebral bodies 2, are driven into the cortical end plates 8 in order to secure the desired position of the prosthesis.

The teeth 6 are arranged in two groups near the ventral and dorsal edges 9 of the connection plate 3, and symmetrically with respect to a diametral axis 10 running in the ventral-dorsal direction. The central tooth of each group is oriented to this diametral direction 10, while the outer-lying teeth enclose an angle α with the diametral direction, which angle is of the order of 30° and should be greater than 20°. The reason for this is that the shearing forces against which the teeth are intended to secure the prosthesis on the vertebral bodies run principally, but not exclusively, in the A-P direction.

Each tooth is delimited by four surfaces, namely by a main surface 11, two side surfaces 13 and a rear surface 12. The main surface 11 runs at an angle of 90° relative to the connection plate 3, more precisely relative to the plane given approximately by the average direction of extension of the tooth-supporting outer surface of the connection plate 3. In the illustrative embodiment, the main surfaces 11 running perpendicular to the connection plate 3 are directed outward (away from the centre of the diametral axis 10). The reverse could also apply.

Figure 6:
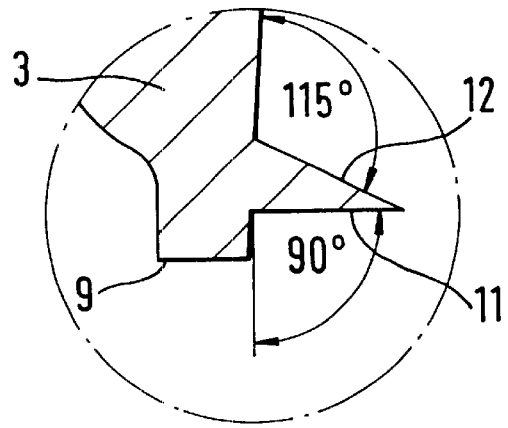

The opposite rear surface 12 runs in a section, parallel to the connection plate, through the tooth parallel to the main surface 11. In the vertical section (FIG. 6) it runs obliquely in relation to the connection plate 3, namely at an angle of 115° in the embodiment shown. This angle is preferably between 105 and 145°.

Figure 5:
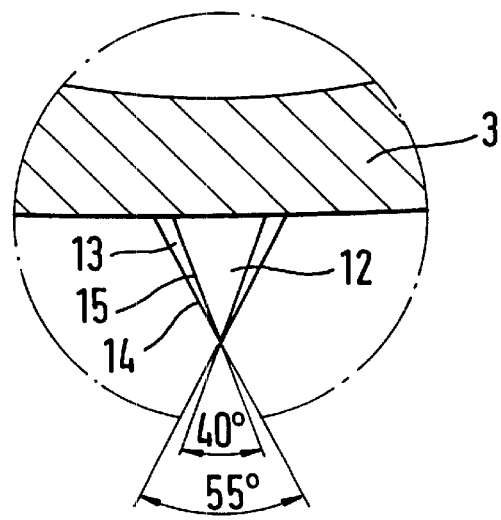

The edges 14, 15 of the main surface 11 and of the rear surface 12 are connected by the side surfaces 13 which are likewise triangular and converge to the same point as the main and rear surfaces 11, 12. In relation to the main surface 11, they run in a section parallel to the connection plate 3 at an acute angle β, which should be smaller than 80°. The edge 14 between the main surface 11 and the side surfaces 13 thus becomes a sort of cutter. The acute angle of the side surfaces 13 relative to the main surface 11 is obtained by the fact that the apex angle of the main surface 11 is slightly greater than that of the rear surface 12. In FIG. 5, these angles have been indicated as 55 and 40°, respectively. The greater the difference between these two angles, the sharper the cutter formed by the edge 14. The apex angle of the main surface 11 should be smaller than 70°, preferably smaller than 60°, while the apex angle of the rear surface is smaller by 10 to 25°, preferably by about 15°.

This has the following effect as the teeth penetrate into the bone cortex of the vertebral bodies. The main surfaces 11 run parallel to the direction of penetration. As soon as the tip of a tooth has passed through the bone cortex, the main surfaces 11 can therefore advance along the initially formed cutting or penetrating edge. The length of this edge increases as penetration progresses, corresponding to the increasing width of the main surface 11. Since this widening takes place in the area of action of the cutter-like edge 14, it has a cutting rather than a breaking action. The bone edge finally cooperating with the main surface 11 is thus substantially free of break damage and therefore better able to take up the forces transmitted by the main surface 11.

By contrast, the penetration of the rear surface 12 and of the side surfaces 13 takes place with progressive displacement of the cooperating edges of the bone cortex. However, this is not a disadvantage since the support of the implant against shearing forces is mainly assumed by the main surface 11.

To ensure a good transmission of forces in all the main directions, the main surfaces 11 of teeth lying diametrally opposite one another are oriented in opposite directions.

Figure 2:
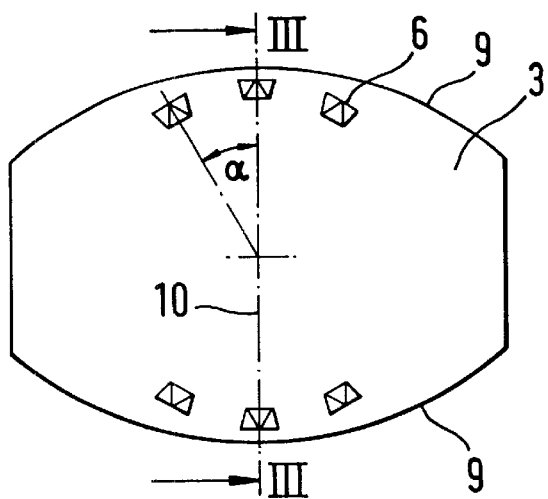
FIG. 2 shows a plan view of the toothed side of a connection plate.
Figure 3:
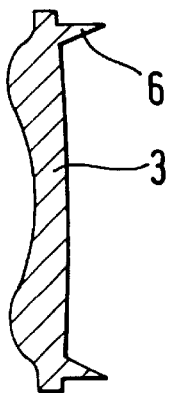
FIG. 3 shows a cross section along the line III—III in FIG. 2.
Figure 4:
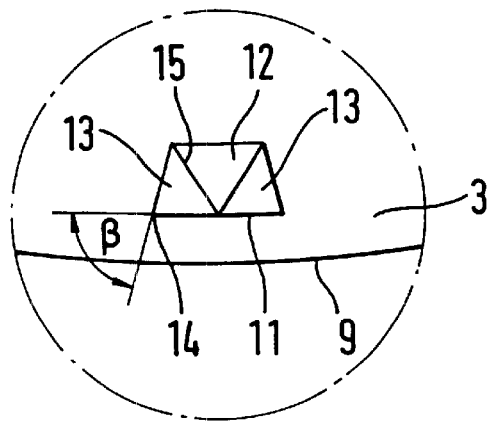
FIGS. 4, 5 and 6 show a plan view and two side views of a tooth in an enlarged representation.

It has been found that the teeth configured according to the invention afford greater security for holding the position of the prosthesis than do the previously known teeth, assuming an approximately identical tooth surface size transverse to the A-P direction 10 (FIG. 2).

What is claimed is:

1. An intervertebral endoprosthesis, comprising a connection plate configured to be fixed on a vertebral surface and to be applied to the vertebral surface in a direction of application that is transverse to a direction of a longer dimension of the connection plate, the connection plate having teeth projecting from a side of the connection plate configured to be fixed on the vertebral surface approximately in the direction of application, another side of the connection plate being configured to engage a core of the intervertebral endoprosthesis, the teeth being defined by surfaces comprising main surfaces arranged in the direction of application, two groups of a plurality of teeth being disposed opposite one another with reference to the direction of a longer dimension of the connection plate, the teeth of one group pointing in directions opposite to directions in which diametrically opposed teeth of the other group point, and the main surfaces of the teeth extending substantially perpendicularly from the side of the connection plate.

2. An intervertebral endoprosthesis, comprising a connection plate configured to be fixed on a vertebral surface and to be applied to the vertebral surface in a direction of application that is transverse to a direction of a longer dimension of the connection plate, the connection plate comprising teeth projecting from a side of the connection plate configured to be fixed on the vertebral surface approximately in the direction of application, each tooth being defined by surfaces comprising a main surface arranged in the direction of application, side surfaces, and a rear surface, two groups of a plurality of teeth being disposed opposite one another with reference to the direction of a longer dimension of the connection plate, the teeth of one group pointing in directions opposite to directions in which diametrically opposed teeth of the other group point, wherein the main surfaces of the teeth of the one group are oriented so as to face away from the main surfaces of the teeth of the other group.

3. The intervertebral endoprosthesis as claimed in claim 2, wherein the main surfaces have sharp edges.

4. The intervertebral endoprosthesis as claimed in claim 3, wherein the teeth have side surfaces that form angles ($\beta$) of not more than 80° with respect to the main surfaces.

5. The intervertebral endoprosthesis as claimed in claim 4, wherein the main surfaces of the teeth are trapezoidal in shape.

6. The intervertebral endoprosthesis as claimed in one of claims 1 through 5, wherein the groups of teeth are provided on opposite edge areas of the connection plate.

7. The intervertebral endoprosthesis as claimed in claim 5, wherein the main surfaces of the teeth of each group are oriented differently at angles ($\alpha$) of at least ±20° in relation to a direction transverse to the direction of a longer dimensional of the connection plate.

8. The intervertebral endoprosthesis as claimed in claim 3, wherein the groups of teeth are provided on opposite edge areas of the connection plate.

9. The intervertebral endoprosthesis as claimed in claim 1, wherein the main surfaces have sharp edges.

10. The intervertebral endoprosthesis of claim 2, wherein an apex angle of the main surface of a tooth differs from an apex angle of the rear surface of said tooth by 10° to 25°.

11. The intervertebral endoprosthesis of claim 2, wherein the main surface of a tooth forms an angle with the connection plate of about 90° and the rear surface of said tooth forms an angle with the connection plate of about 105° to 145°.

12. The intervertebral endoprosthesis of claim 2, wherein an apex angle of the main surface of a tooth differs from an apex angle of the rear surface of said tooth by about 15°.

13. The intervertebral endoprosthesis of claim 2, wherein the main surface of a tooth forms an angle with the connection plate of about 90° and the rear surface of said tooth forms an angle with the connection plate of about 115°.

* * * * *

UNITED STATES PATENT AND TRADEMARK OFFICE
CERTIFICATE OF CORRECTION

PATENT NO.    : 6,416,551 B1
DATED         : July 9, 2002
INVENTOR(S)   : Hoeppner et al.

It is certified that error appears in the above-identified patent and that said Letters Patent is hereby corrected as shown below:

Title page,
Item [56], References Cited, OTHER DOCUMENTS, delete "US 5,387,242 02/1995, Miser (withdrawn)".

Column 7,
Line 5, "tibia" should be -- tibial --.
Line 7, "Ti-6Al-4V" should be -- Ti-6A1-4V --.

Column 10,
Line 5, "by" should be -- be --.

Column 17,
Line 20, after "376" insert -- is --.

Signed and Sealed this

Twenty-fifth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,416,551 B1
DATED        : July 9, 2002
INVENTOR(S)  : Arnold Keller It is certified that error appears in the above-identified patent and that said Letters Patent is hereby corrected as shown below:

This certificate supersedes Certificate of Correction issued February 25, 2003, the number was erroneously mentioned and should be vacated since no Certificate of Correction was granted.

Signed and Sealed this

Fifteenth Day of April, 2003

JAMES E. ROGAN
*Director of the United States Patent and Trademark Office*